United States Patent [19]

Lin

[11] 4,391,751
[45] Jul. 5, 1983

[54] PHTHALIC ANHYDRIDE DERIVATIVES

[75] Inventor: Chung-Yuan Lin, Northford, Conn.

[73] Assignee: The Upjohn Company, Kalamazoo, Mich.

[21] Appl. No.: 356,047

[22] Filed: Mar. 8, 1982

[51] Int. Cl.³ .............. C07D 401/06; C07D 403/06; C08G 69/16
[52] U.S. Cl. ..................... 260/239.3 R; 544/318; 548/318; 528/271; 528/350
[58] Field of Search .............. 260/239.3 R; 544/318; 548/318; 528/271, 350

[56] References Cited

U.S. PATENT DOCUMENTS 3,428,486 2/1969 George ............................. 528/350
3,817,442 6/1974 Kovacs et al. ..................... 528/350

Primary Examiner—Robert T. Bond
Attorney, Agent, or Firm—Denis A. Firth; John Kekich

[57] ABSTRACT

Compounds are described which are characterized by the formula

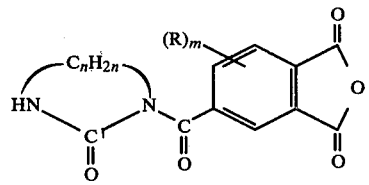

$C_nH_{2n}$=alkylene with 2 to 6 C atoms in the chain.
R=inert substituent and m=0-3.

The compounds contain an anhydride group and a hetero ring capable of opening to yield an isocyanate group on heating. Accordingly, they can undergo self-condensation on heating to yield polyamide-imides. The compounds can also be polymerized by heating in the presence of difunctional monomers such as diols, diamines, alkanolamines and the like.

9 Claims, No Drawings

PHTHALIC ANHYDRIDE DERIVATIVES

BACKGROUND OF THE INVENTION

1. Field of the Invention

This invention relates to novel heterocyclic compounds and methods for their preparation and is more particularly concerned with compounds which contain both an anhydride group and a hetero ring which can dissociate on heating to yield an isocyanate group, and with polymers derived from said compounds by self-condensation and or by copolymerization in the presence of additional polyfunctional monomers.

2. Description of the Prior Art

Various types of compounds have been described which can undergo self-condensation to generate polymers. Illustratively, U.S. Pat. No. 3,951,922 describes isocyanato-phthalic anhydrides which, upon heating, undergo self-condensation to form polyimides. The conversion of caprolactam to polyamides is, of course, a well-recognized and widely practiced commercial process which involves generation of a polymer from a single monomer and can be broadly regarded as self-condensation.

A somewhat related process is that described in U.S. Pat. No. 4,138,398 in which certain bis(cyclic ureas) are utilized as blocked isocyanates insofar as they undergo ring-opening to form diisocyanates upon heating. By heating a mixture of stoichiometric amounts of these bis(cyclic ureas) and an appropriate polyol, which mixture is stable upon storage until utilized, it is possible to prepare polyurethanes.

I have now found a novel class of compounds which contain, in the same molecule, a dicarboxylic acid anhydride group and a hetero ring (cyclic urea) which will undergo ring opening to yield an isocyanato group upon heating to the appropriate temperature. This combination of groups in the same molecule enables the compounds in question to undergo self-condensation upon heating. It also enables the production of a considerable range of novel copolymers by conducting the self-condensation reaction in the presence of difunctional or polyfunctional monomers which contain groups reactive with either isocyanato groups or dicarboxylic acid anhydride groups or both.

SUMMARY OF THE INVENTION

This invention comprises novel compounds having the formula:

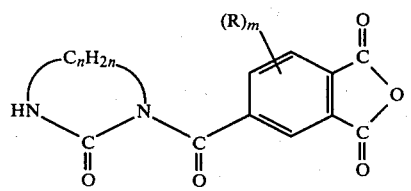

wherein $C_nH_{2n}$ represents alkylene containing from 2 to 6 carbon atoms in the chain separating the valencies, R is an inert substituent and m is an integer from 0 to 3.

The invention also comprises copolymers derived from the above compounds (I) by self-condensation of the said compounds alone or in the presence of difunctional or polyfunctional monomers which contain groups reactive with isocyanato groups and or with dicarboxylic acid anhydride groups.

The term "alkylene containing from 2 to 6 carbon atoms in the chain separating the valencies" means straight or branched chain alkylene having the stated number of C atoms in the chain, and is inclusive of ethylene, trimethylene, tetramethylene, pentamethylene, hexamethylene, 2-ethyltrimethylene, 2,2-dimethyltetramethylene, 1,2-hexylene, 1,2-octylene, 2,3,4-trimethyl-pentamethylene, and the like.

The term "inert substituent" means a substituent which is chemically inert under the reaction conditions required to prepare the compounds (I) as hereinafter described. Exemplary of such substituents are:

lower-alkyl, i.e. alkyl having from 1 to 6 carbon atoms inclusive such as methyl, ethyl, propyl, butyl, pentyl, hexyl and isomeric forms thereof; lower-alkoxy, i.e. alkoxy having from 1 to 6 carbon atoms such as methoxy, ethoxy, propoxy, butoxy, pentyloxy, hexyloxy and isomeric forms thereof; lower-alkenyl, i.e. alkenyl from 2 to 6 carbon atoms such as vinyl, propenyl, butenyl, pentenyl, hexenyl and isomeric forms thereof; lower-alkylmercapto, i.e. alkylmercapto having from 1 to 6 carbon atoms such as methylmercapto, ethylmercapto, propylmercapto, butylmercapto, pentylmercapto, hexylmercapto and isomeric forms thereof; lower-alkenyloxy, i.e. alkenyloxy having from 3 to 6 carbon atoms such as propenyloxy, butenyloxy, pentenyloxy, hexenyloxy and isomeric forms thereof; cyano; and trifluoromethyl.

The nomenclature which will be employed throughout this specification and claims to designate the individual compounds characterized by the formula (I) above is illustrated by the following example. Thus, the species corresponding to the formula:

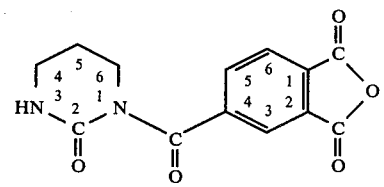

is designated as 4-(N,N'-trimethyleneallophanyl)phthalic anhydride.

DETAILED DESCRIPTION OF THE INVENTION

The compounds of the invention having the formula (I) are conveniently prepared by reaction of the appropriate cyclic urea having the formula (II) with the appropriate acid halide having the formula (III) in accordance with the reaction shown schematically as follows:

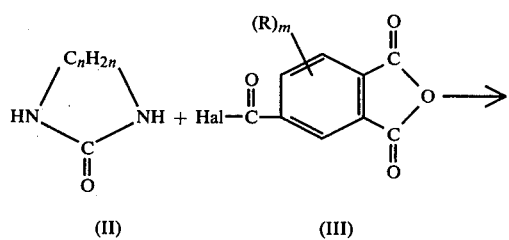

(I) + H—Hal

In the above formulae the parameters $C_nH_{2n}$, R and m have the meaning hereinbefore defined and Hal represents halogen preferably chlorine or bromine. The reaction is advantageously carried out in the presence of an inert organic solvent and a base. By "inert organic solvent" is meant an organic solvent which does not enter into reaction with any of the reactants employed or interfere in any other manner with the desired course of the reaction. Illustrative of inert organic solvents are benzene, toluene, xylene, chlorobenzene, dichlorobenzene, tetralin, acetonitrile, tetramethylene sulfone, methylene chloride, chloroform, ethylene chloride and the like.

Any base capable of removing hydrohalic acids (generated in the above condensation) can be employed as the base in the above process. Such bases include inorganic bases such as sodium hydroxide, potassium hydroxide, calcium carbonate and the like, as well as tertiary organic bases such as pyridine, triethylamine, tributylamine, N,N-dimethylaniline and the like.

The above reaction can be carried out over a wide range of temperatures from about 0° C. to about 100° C. and proceeds steadily and smoothly even at temperatures in the lower end of this range. The progress of the reaction can be followed by routine analytical techniques such as infrared spectroscopy, nuclear magnetic resonance spectroscopy, and the like.

When the reaction is adjudged complete by any of the analytical techniques in question, the desired compound (I) can be isolated from the reaction mixture by conventional techniques. For example, the excess base plus hydrohalide salt can be removed by aqueous extraction, filtration or like techniques and the inert organic solvent can then be removed by distillation. The compound (I) which remains as the residue can be purified, if desired, by conventional techniques such as re-crystallization, chromatography and the like.

The cyclic ureas (II) which are employed as starting materials to prepare the compounds (I) of the invention are, for the most part, known compounds and can be prepared by conventional procedures for the synthesis of cyclic ureas; see, for example, Ozaki et al., J. Amer. Chem. Soc., 79, 4358, 1957; see also the review by Peterson, Synthesis (International Journal of Methods in Synthetic Organic Chemistry), May 1973, pp. 243–292, which gives details of the preparation of cyclic ureas by a variety of methods and, at pages 271–2, gives a list of dihydro-2(1H)-pyrimidinones which can be subjected to catalytic hydrogenation using conventional techniques to yield the corresponding tetrahydro-2(1H)-pyrimidinones. Illustrative of the cyclic ureas (II) are the following: 2-imidazolidinone; 4,4-dimethyl-, 4,5-dimethyl-, 4-butyl-, 4-hexyl-, 4-propyl-, and 4,5,5-trimethyl-imidazolidinones; 3,4,5,6-tetrahydro-2(1H)-pyrimidinone; 4-methyl-, 5-methyl-, 5,5-dimethyl-, 4,4,6-trimethyl-, and 4-isopropyl-5,5-dimethyl-3,4,5,6-tetrahydro-2 (1H)pyrimidinones; N,N'-tetramethyleneurea, N,N'-pentamethyleneurea, N,N'-hexamethyleneurea, N,N'-2-methyltetramethyleneurea, N,N'-2,2-dimethyltetramethyleneurea, N,N'-2,3-diethyltetramethyleneurea, and N,N'-2,2-dimethylpentamethyleneurea.

The acid halides (III) which are employed in the preparation of the compounds (I) of the invention are well-known in the art. Illustrative of said compounds are the acid chlorides and acid bromides of trimellitic anhydride, 3,5-dimethyl-, 3-methoxy-, 3,5-dimethoxy-, 3,5,6-trimethyl-, and 3,5,6-trimethoxybenzene-1,2,4-tricarboxylic acid anhydride.

As previously stated, the compounds of the invention (I) undergo self-condensation to form polyamide-imides on heating. The temperature to which it is necessary to heat any given compound in order to initiate the self-condensation varies but is generally within the range of about 100° C. to about 300° C. or higher. The self-condensation reaction is illustrated schematically as follows.

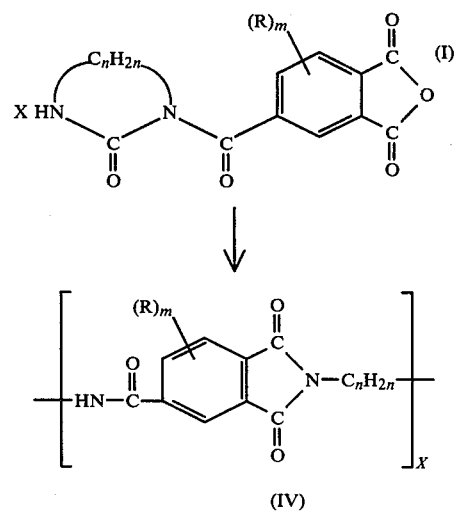

The self-condensation can be carried out in the presence or absence of an inert organic solvent. If desired a catalyst such as sodium methoxide, potassium methoxide, sodium ethoxide and like bases, can be employed in the reaction but is not essential to effect the self-condensation.

The polyamide-imides, having the recurring unit (IV), which are so obtained are characterized by good physical properties including structural strength properties and can be molded using conventional techniques such as injection molding, compression molding and the like to give articles such as bushings, seal faces, electric insulators, compressor vanes and impellers, pistons and piston rings, gears, thread guides, cams, brake linings, clutch faces, abrasive articles and the like.

If the self-condensation reaction is carried out in the presence of di- or higher functional compounds, i.e. compounds containing two or more hydroxyl, amino, carboxy, isocyanato groups or a mixture of two or more such groups, there are obtained polymers which contain additional moieties which serve to modify the properties of the resulting polymers. The nature of the polymers so prepared will obviously depend to a great extent on the nature of the polyfunctional compound employed and on the proportion of polyfunctional compound to compound (I) employed in the polymerization. Illustrative of polyfunctional compounds which can be employed are polyols, aminoalcohols, diamines, polyamines, di- and polyisocyanates, di- and polycarboxylic acids and anhydrides thereof, and the like.

The polymers derived from the compounds of the invention (I) can have incorporated in them, by any of the methods conventional in the art, additives such as pigments, fillers, lubricants, stabilizers, antioxidants, coloring agents, fire retardants and the like, which are commonly employed in conjunction with polyamide-imides and related polymers.

The following examples describe the manner and process of making and using the invention and set forth the best mode contemplated by the inventor of carrying out the invention but are not to be construed as limiting.

EXAMPLE 1

4-(N,N'-trimethyleneallophanyl)phthalic anhydride

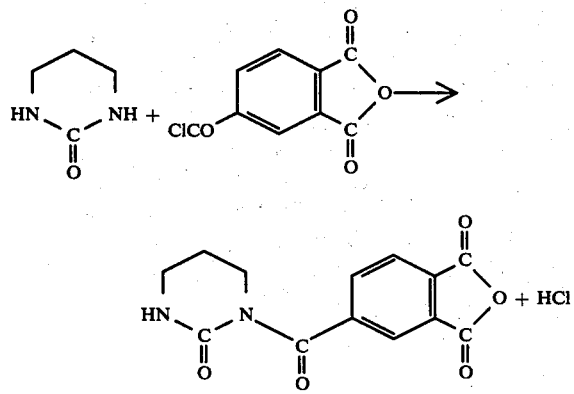

A solution of 52.65 g. (0.25 mole) of trimellitic anhydride acid chloride (previously redistilled under reduced pressure) in 100 ml. of methylene chloride was added, slowly with stirring, to a suspension of 26.25 g. (0.262 mole) of 3,4,5,6-tetrahydro-2(1H)pyrimidinone and 20.75 g. (0.262 mole) of pyridine in 150 ml. of methylene chloride. The addition was made at room temperature (circa 20° C.) over a period of 2 hours. After the addition was complete, the reaction mixture was stirred for a further 3.0 hr. at the same temperature and then allowed to stand overnight. At the end of this time the mixture was filtered and the solid so isolated was washed on the filter with water and then with tetrahydrofuran before being dried in vacuo to yield 47.6 g. of 4-(N,N'-trimethyleneallophanyl)phthalic anhydride in the form of a crystalline solid having a melting point of 215°–218° C. Further washing with tetrahydrofuran followed by vacuum drying raised the melting point to 218°–221° C. A final washing with methanol followed by vacuum drying gave 37.5 g. of product (54.7 percent yield) having a melting point of 229° to 233° C. (with decomposition). The structure of the compound was confirmed by nuclear magnetic resonance analysis.

EXAMPLE 2

4-(N,N'-ethyleneallophanyl)phthalic anhydride

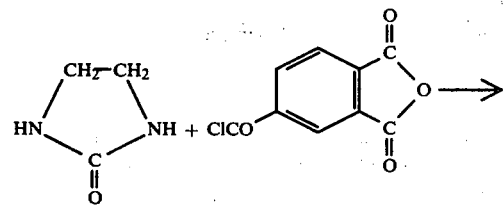

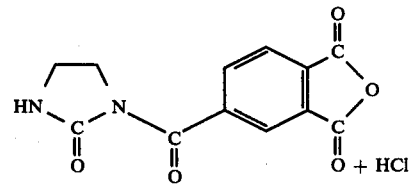

A solution of 10.53 g. (0.05 mole) of trimellitic anhydride acid chloride (previously redistilled under reduced pressure) in 20 ml. of methylene chloride was added slowly to a stirred suspension of 4.73 g. (0.055 mole) of 2-imidazolidinone (freshly recrystallized from chloroform) and 4.35 g. (0.055 mole) of pyridine in 50 ml. of methylene chloride. The addition was completed in 2 hours at room temperature (circa 20° C.). Thereafter the mixture was stirred for a further 3 hours at the same temperature before being filtered. The solid so isolated was washed on the filter with water and then with tetrahydrofuran before being dried in vacuo. There was thus obtained 11.8 g. (91 percent yield) of 4-(N,N'-ethyleneallophanyl)phthalic anhydride in the form of a yellow solid having a melting point of 273°–6° C. (with decomposition). The identity of the compound was confirmed by nuclear magnetic resonance analysis.

EXAMPLE 3

4-(N,N'-tetramethyleneallophanyl)phthalic anhydride

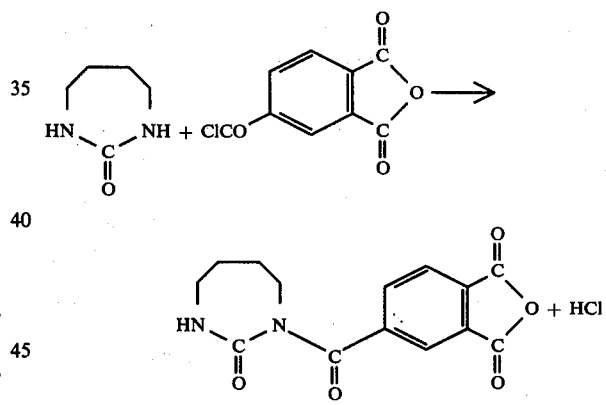

A solution of 10.53 g. (0.05 mole) of trimellitic anhydride acid chloride (previously redistilled under reduced pressure) in 20 ml. of methylene chloride was added slowly with stirring to a solution of 6.37 g. (0.055 mole) of N,N'-tetramethyleneurea and 4.35 g. (0.055 mole) of pyridine in 50 ml. of methylene chloride. The addition was completed in 2 hours at room temperature (circa 20° C.) and thereafter the mixture was stirred for a further 3 hours at the same temperature. The resulting solution was extracted with water before being dried over anhydrous magnesium sulfate. The dried solution was evaporated to dryness and the residue was treated with ethylene chloride. The white solid which separated was isolated by filtration and dried in vacuo. There was thus obtained 10 g. (69 percent yield) of 4-(N,N'-tetramethyleneallophanyl)phthalic anhydride in the form of a white powder having a melting point of 190°–193° C. (with decomposition). The identity of the compound was confirmed by nuclear magnetic resonance analysis.

EXAMPLE 4

4-(N,N'-pentamethyleneallophanyl)phthalic anhydride

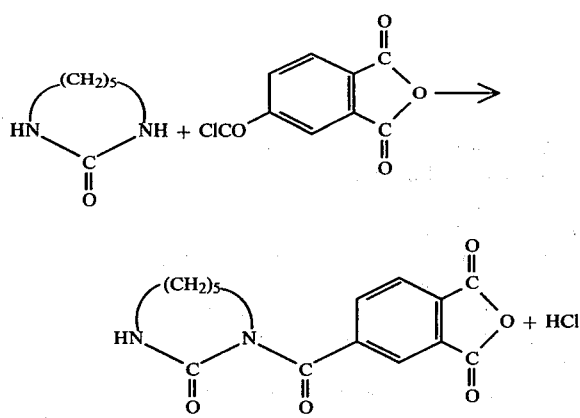

A solution of 10.53 g. (0.05 mole) of trimellitic anhydride acid chloride (previously redistilled under reduced pressure) in 20 ml. of methylene chloride was added, with stirring, over a period of 2 hours to a suspension of 6.72 g. (0.0525 mole) of N,N'-pentamethyleneurea and 4.35 g. (0.055 mole) of pyridine in 50 ml. of methylene chloride. The addition was made at room temperature (circa 20° C.) and, when it was complete, the mixture was stirred for a further 3 hours at the same temperature. The resulting product was a clear solution which was then cooled in an ice bath. The solid which separated was isolated by filtration, washed with water and dried in vacuo at 80° C. There was thus obtained 13.5 g. of 4-(N,N'-pentamethyleneallophanyl)phthalic anhydride in the form of a white granular solid having a melting point of 168°–173° C. The nuclear magnetic resonance spectrum revealed the presence of ca 1/6 mole percent of methylene chloride combined with the product, which solvent could not be removed by further drying.

EXAMPLE 5

Using the procedure described in Example 1 but replacing the trimellitic anhydride acid chloride there used by an equivalent amount of the acid chlorides of 3,5-dimethyl-, 3-methoxy-, 3,5-dimethoxy-, 3,5,6-trimethyl-, and 3,5,6-trimethoxybenzene-1,2,4-tricarboxylic acid anhydride there are obtained 3,5-dimethyl-, 3-methoxy-, 3,5-dimethoxy-, 3,5,6-trimethyl- and 3,5,6-trimethoxy-4-(N,N'-trimethyleneallophanyl)phthalic anhydrides, respectively.

EXAMPLE 6

A mixture of 1.5 g. of 4-(N,N'-trimethyleneallophanyl)phthalic anhydride [prepared as described in Example 1], 0.015 g. of sodium methoxide and 10 g. of tetramethylenesulfone was stirred under an atmosphere of nitrogen and heated at 160° C. for 1 hour followed by 1 hour at 190° C. and, finally, 1 hour at 230° C. The resulting mixture was allowed to cool partially and poured slowly, while still hot, into 200 ml. of methanol. The solid which separated was isolated by filtration, washed with methanol and dried in vacuo. There was obtained a polymer characterized by a recurring unit of the formula:

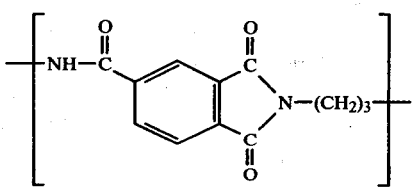

and having an inherent viscosity η at 30° C. (0.5 percent in conc. sulfuric acid) of 0.87. A Gehman plot (ASTM-D 1053-85T) of shear modulus versus temperature on a test bar, obtained by compression molding at 250° C. of the above material, showed that the polymer is injection moldable at or below 250° C. (3G=6.48×10$^5$ dynes/cm$^2$ at 235° C.). A differential scanning calorimetric determination showed a Tg=175° C. Thermal gravimetric analysis in nitrogen showed that no significant weight loss occurred until the temperature reached 375° C. At 400° C. the weight loss was 10 percent, at 450° C. it was 33 percent and at 500° C. it was 38 percent.

EXAMPLE 7

Using the procedure described in Example 6 but replacing the starting material there used by 1.5 g. of 4-(N,N'-tetramethyleneallophanyl)phthalic anhydride [prepared as described in Example 3] there was obtained the corresponding polymer characterized by a recurring unit of the formula:

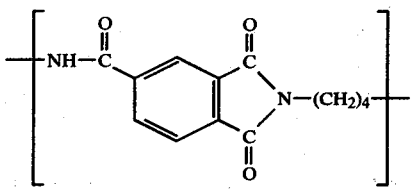

The polymer was found to have an inherent viscosity η at 30° C. (0.5 percent in conc. sulfuric acid) of 0.71.

EXAMPLE 8

Using the procedure described in Example 6 but replacing the starting material there used by 1.5 g. of 4-(N,N'-pentamethyleneallophanyl)phthalic anhydride [prepared as described in Example 4] there was obtained the corresponding polymer characterized by a recurring unit of the formula:

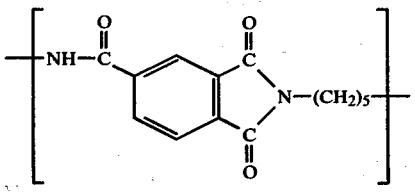

The polymer was found to have an inherent viscosity η at 30° C. (0.5 percent in conc. sulfuric acid) of 0.96.

I claim:

1. A compound having the formula

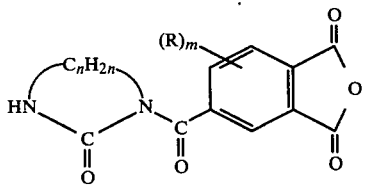

wherein $C_nH_{2n}$ represents alkylene containing from 2 to 6 carbon atoms in the chain separating the valencies, R is an inert substituent selected from the class consisting of lower-alkyl, lower-alkoxy, lower-alkenyl, lower-alkenyloxy, lower-alkylmercapto, cyano and trifluoromethyl, and m is an integer from 0 to 3.

2. A compound according to claim 1 wherein $C_nH_{2n}$ is ethylene and m=0, said compound being 4-(N,N'-ethyleneallophanyl)phthalic anhydride corresponding to the formula:

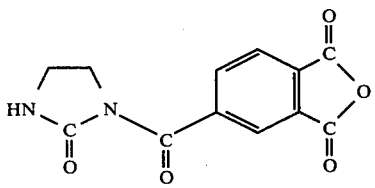

3. A compound according to claim 1 wherein $C_nH_{2n}$ is trimethylene and m=0, said compound being 4-(N,N'-trimethyleneallophanyl)phthalic anhydride corresponding to the formula:

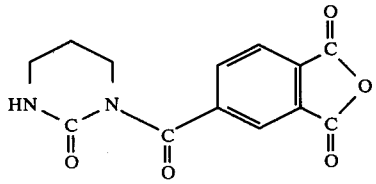

4. A compound according to claim 1 wherein $C_nH_{2n}$ is tetramethylene and m=0, said compound being 4-(N,N'-tetramethyleneallophanyl)phthalic anhydride corresponding to the formula:

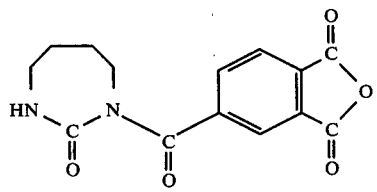

5. A compound according to claim 1 wherein $C_nH_{2n}$ is pentamethylene and m=0, said compound being 4-(N,N'-pentamethyleneallophanyl)phthalic anhydride corresponding to the formula:

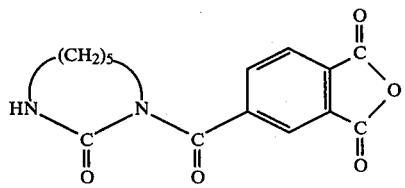

6. A process for the preparation of a polymer characterized by the recurring unit

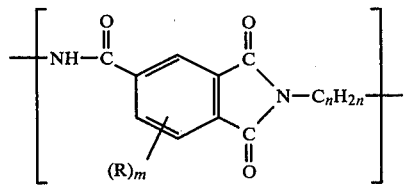

wherein $C_nH_{2n}$ represents alkylene containing from 2 to 6 carbon atoms in the chain separating the valencies, R is an inert substituent selected from the class consisting of lower-alkyl, lower-alkoxy, lower-alkenyl, lower-alkenyloxy, lower-alkylmercapto, cyano and trifluoromethyl, and m is an integer from 0 to 3, which process comprises heating, to a temperature in the range of 100° C. to 300° C., a compound according to claim 1.

7. A process according to claim 6 wherein the heating is carried out in the presence of an inert organic solvent.

8. A process according to claim 6 or 7 wherein the heating is carried out in the presence of a catalyst.

9. A process according to claim 6 wherein the heating is carried out in the presence of a polyfunctional compound containing at least two groups which will enter into reaction with isocyanato groups and or dicarboxylic acid anhydride groups.

* * * * *

UNITED STATES PATENT OFFICE
CERTIFICATE OF CORRECTION

Patent No. 4,391,751  Dated July 5, 1983

Inventor(s) Chung-Yuan Lin

It is certified that error appears in the above-identified patent and that said Letters Patent are hereby corrected as shown below:

On the title page: Under "References Cited-U.S. PATENT DOCUMENTS" "3,817,442" should read --3,817,942--.
Column 1, line 63: "copolymers" should read --polymers--.

Signed and Sealed this

Twentieth Day of September 1983

[SEAL]

Attest:

Attesting Officer

GERALD J. MOSSINGHOFF

Commissioner of Patents and Trademarks